US012644106B2

(12) United States Patent
Wu et al.

(10) Patent No.: US 12,644,106 B2
(45) **Date of Patent: \*Jun. 2, 2026**

---

(54) PHYTASE MUTANT

(71) Applicant: QINGDAO VLAND BIOTECH GROUP CO., LTD., Qingdao (CN)

(72) Inventors: Xiuxiu Wu, Qingdao (CN); Xinpei Li, Qingdao (CN); Rui Li, Qingdao (CN); Qingqing Song, Qingdao (CN); Yijun Huang, Qingdao (CN)

(73) Assignee: QINGDAO VLAND BIOTECH GROUP CO., LTD., Qingdao (CN)

( * ) Notice: Subject to any disclaimer, the term of this patent is extended or adjusted under 35 U.S.C. 154(b) by 649 days.

This patent is subject to a terminal disclaimer.

(21) Appl. No.: 17/927,023

(22) PCT Filed: May 20, 2021

(86) PCT No.: PCT/CN2021/094767
§ 371 (c)(1),
(2) Date: Nov. 22, 2022

(87) PCT Pub. No.: WO2021/233361
PCT Pub. Date: Nov. 25, 2021

(65) Prior Publication Data
US 2023/0242890 A1      Aug. 3, 2023

(30) Foreign Application Priority Data

May 22, 2020      (CN) ......................... 202010442538.3
Dec. 29, 2020      (CN) ......................... 202011596375.0

(51) Int. Cl.
*C12N 9/16*      (2006.01)
*C12N 1/21*      (2006.01)

(52) U.S. Cl.
CPC ........ *C12N 9/16* (2013.01); *C12Y 301/03008* (2013.01)

(58) Field of Classification Search
None
See application file for complete search history.

(56) References Cited

U.S. PATENT DOCUMENTS 9,879,238 B2      1/2018   Tan et al.
2020/0277582 A1 *   9/2020   Wu ......................... C12N 15/81

2020/0299709 A1 *   9/2020   Raab .................... A23K 20/158
2021/0207112 A1 *   7/2021   Bai .......................... C12N 9/16
2022/0154154 A1      5/2022   Wu et al.

FOREIGN PATENT DOCUMENTS

| CN | 107236717 A | 10/2017 | |
| EP | 3222714 A1 * | 9/2017 | ............... C12N 9/16 |
| EP | 3438253 A1 | 2/2019 | |
| WO | 2010/135588 A2 | 11/2010 | |
| WO | WO-2017166562 A1 * | 10/2017 | ............. C12N 15/81 |
| WO | 2019/228441 A1 | 12/2019 | |
| WO | 2020063267 A1 | 4/2020 | |
| WO | 2020063268 A1 | 4/2020 | |
| WO | 2020168943 A1 | 8/2020 | |

OTHER PUBLICATIONS

English language machine translation of WO 2017166562 A1, 2017. (Year: 2017).*
International Search Report for PCT/CN2021/094767 mailed Jul. 30, 2021, ISA/CN.
Wang, X et al., "Enzymology and thermal stability of phytase appA mutants", RSC Advances, vol. 5, No. 54,Dec. 31, 2015 (Dec. 31, 2015), ISSN: 2046-2069, pp. 43863-43872, abstract.
Zhou, Yuling et al., "High-Level Expression and Characteristics of A Thermostable Phytase Mutant from *Escherichia coli* KI2 in Pichia Pastoris", Chemistry & Bioengineering, vol. 30 . No. 2. Feb. 25, 2013 (Feb. 25, 2013), ISSN: 1674-5425, pp. 36-42, entire document.
Search Report dated May 29, 2024 for European patent application No. 21809654.3.

* cited by examiner

*Primary Examiner* — Todd M Epstein

(74) *Attorney, Agent, or Firm* — Yue (Robert) Xu; Apex Attorneys at Law, LLP

(57)      ABSTRACT

Provided are a phytase mutant and a coding DNA molecule thereof, a vector, and a host cell. The phytase mutant comprises an amino acid sequence having at least 90% identity with SEQ ID NO: 3, and compared with SEQ ID NO: 3, and contains an amino acid substitution at at least one position selected from the group consisting of 36, 126, 211, 253, 258, and 266. The heat resistance of the mutant is significantly improved, thus facilitating the wide application of phytase in feed.

9 Claims, No Drawings
Specification includes a Sequence Listing.

SEQUENCE LISTING

<160> NUMBER OF SEQ ID NOS: 28

<210> SEQ ID NO 1
<211> LENGTH: 410

<212> TYPE: PRT
<213> ORGANISM: Escherichia coli

<400> SEQUENCE: 1

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400
```

-continued

```
Asn Glu Ala Arg Ile Pro Ala Cys Ser Leu
            405                 410

<210> SEQ ID NO 2
<211> LENGTH: 1233
<212> TYPE: DNA
<213> ORGANISM: Escherichia coli

<400> SEQUENCE: 2
cagagtgagc cggagctgaa gctggaaagt gtggtgattg tcagtcgtca tggtgtgcgt      60
gctccaacca aggccacgca actgatgcag gatgtcaccc cagacgcatg gccaacctgg     120
ccggtaaaac tgggttggct gacaccgcgc ggtggtgagc taatcgccta tctcggacat     180
taccaacgcc agcgtctggt agccgacgga ttgctggcga aaaagggctg cccgcagtct     240
ggtcaggtcg cgattattgc tgatgtcgac gagcgtaccc gtaaaacagg cgaagccttc     300
gccgccgggc tggcacctga ctgtgcaata accgtacata cccaggcaga tacgtccagt     360
cccgatccgt tatttaatcc tctaaaaact ggcgtttgcc aactggataa cgcgaacgtg     420
actgacgcga tcctcagcag ggcaggaggg tcaattgctg actttaccgg gcatcggcaa     480
acggcgtttc gcgaactgga acgggtgctt aattttccgc aatcaaactt gtgccttaaa     540
cgtgagaaac aggacgaaag ctgttcatta acgcaggcat taccatcgga actcaaggtg     600
agcgccgaca atgtctcatt aaccggtgcg gtaagcctcg catcaatgct gacggagata     660
tttctcctgc aacaagcaca gggaatgccg gagccggggt ggggaaggat caccgattca     720
caccagtgga acaccttgct aagtttgcat aacgcgcaat tttatttgct acaacgcacg     780
ccagaggttg cccgcagccg cgccaccccg ttattagatt tgatcaagac agcgttgacg     840
ccccatccac cgcaaaaaca ggcgtatggt gtgacattac ccacttcagt gctgtttatc     900
gccggacacg atactaatct ggcaaatctc ggcggcgcac tggagctcaa ctggacgctt     960
cccggtcagc cggataacac gccgccaggt ggtgaactgg tgtttgaacg ctggcgtcgg    1020
ctaagcgata acagccagtg gattcaggtt tcgctggtct tccagacttt acagcagatg    1080
cgtgataaaa cgccgctgtc attaaatacg ccgcccggag aggtgaaact gaccctggca    1140
ggatgtgaag agcgaaatgc gcagggcatg tgttcgttgg caggttttac gcaaatcgtg    1200
aatgaagcac gcataccggc gtgcagtttg taa                                 1233

<210> SEQ ID NO 3
<211> LENGTH: 410
<212> TYPE: PRT
<213> ORGANISM: Artificial Sequence
<220> FEATURE:
<223> OTHER INFORMATION: Phytase mutant

<400> SEQUENCE: 3

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80
```

-continued

```
Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
        130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 4
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 4
caatctgaac cagaattgaa gttggaatct gttgttattg tttcccgtca cggtgttaga        60
gccccaacta aggctactca attgatgcaa gatgttactc cagatgcttg gccaacttgg       120
ccagttaagt tgggtgaatt gactccaaga ggtggtgaat tgattgctta cttgggtcat       180
```

-continued

```
tactggagac aaagattggt tgctgatgaa ttgttgccaa agaagggttg tccacaatct      240
ggtcaagttg ctattattgc tgatgttgat gaacgcacta gaaagaccgg tgaggctttt      300
gctgctggtt tggctccaga ttgtgctatt actgttcatc atcaagctga tacttcttcc      360
ccagatccat tgtttaaccc attgaagact ggtgtttgtc aattggatgt tgctaacgtt      420
actagagcta ttttggaaag agctggtggt tctattgctg attttactgg tcattaccaa      480 accgccttc gtgaattgga aagagttttg aactttccac aatccaactt gtgtttgaag       540
agagaaaagc aagatgagtc ctgttccttg acccaagctc ttccatctga attgaaggtt      600
tctgctgata cgtttctttt gactggtgct gtttctttgg cttctatgtt gactgaaatt      660
ttcttgttgc agcaggctca aggtatgcca gaaccaggtt ggggtagaat tactgattct      720
catcaatgga cactttgtt gtctttgcat aacgctcaat ttgacttgtt gcaaagaact        780
ccagaagttg ctagatctag agctactcca ttgttggatt tgattaagac tgctttgact      840
ccacatccac cacaaaagca ggcttacggt gttactttgc caacttctgt tttgtttatt      900
gccggtcatg ataccaactt ggctaacttg ggtggtgctt tggaattgaa ctggactttg      960
ccaggtcaac cagataacac tccaccaggt ggtgaattgg tttttgaaag atggagaaga     1020
ttgtccgata actctcaatg gattcaagtt tctttggtct ttcagacctt gcagcaaatg     1080
agagataaga ctccattgtc tttgaacact ccaccaggtg aagttaagtt gactttggct     1140
ggttgtgaag aaagaaacgc tcaaggtatg tgttctttgg ctggttttac tcaaattgtc     1200
aacgaggcta gaatcccagc ttgttctttg                                      1230
```

<210> SEQ ID NO 5
<211> LENGTH: 410
<212> TYPE: PRT
<213> ORGANISM: Artificial Sequence
<220> FEATURE:
<223> OTHER INFORMATION: Phytase mutant

<400> SEQUENCE: 5

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Pro Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175
```

```
Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410
```

<210> SEQ ID NO 6
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 6

```
caatctgaac cagaattgaa gttggaatct gttgttattg tttcccgtca cggtgttaga      60
gccccaacta aggctactca attgatgcaa gatgttactc cagatccatg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat gttttaaccc attgaagact ggtgtttgtc aattggatgt tgctaacgtt     420
actagagcta tttttggaaag agctggtggt tctattgctg attttactgg tcattaccaa     480
accgcctttc gtgaattgga aagagttttg aactttccac aatccaactt gtgtttgaag     540
agagaaaagc aagatgagtc ctgttccttg acccaagctc ttccatctga attgaaggtt     600
tctgctgata cgtttctttt gactggtgct gtttctttgg cttctatgtt gactgaaatt     660
ttcttgttgc agcaggctca aggtatgcca gaaccaggtt ggggtagaat tactgattct     720
```

```
catcaatgga acactttgtt gtctttgcat aacgctcaat ttgacttgtt gcaaagaact      780
ccagaagttg ctagatctag agctactcca ttgttggatt tgattaagac tgctttgact      840
ccacatccac cacaaaagca ggcttacggt gttactttgc caacttctgt tttgtttatt      900
gccggtcatg ataccaactt ggctaacttg ggtggtgctt tggaattgaa ctggactttg      960
ccaggtcaac cagataacac tccaccaggt ggtgaattgg tttttgaaag atggagaaga     1020
ttgtccgata actctcaatg gattcaagtt tctttggtct ttcagacctt gcagcaaatg     1080
agagataaga ctccattgtc tttgaacact ccaccaggtg aagttaagtt gactttggct     1140
ggttgtgaag aaagaaacgc tcaaggtatg tgttctttgg ctggttttac tcaaattgtc     1200
aacgaggcta gaatcccagc ttgttctttg                                      1230
```

```
<210> SEQ ID NO 7
<211> LENGTH: 410
<212> TYPE: PRT
<213> ORGANISM: Artificial Sequence
<220> FEATURE:
<223> OTHER INFORMATION: Phytase mutant

<400> SEQUENCE: 7

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Glu Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270
```

-continued

```
Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 8
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 8
caatctgaac cagaattgaa gttggaatct gttgttattg tttcccgtca cggtgttaga      60
gccccaacta aggctactca attgatgcaa gatgttactc cagatgcttg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat tgtttgagcc attgaagact ggtgtttgtc aattggatgt tgctaacgtt     420
actagagcta ttttggaaag agctggtggt tctattgctg attttactgg tcattaccaa     480
accgcctttc gtgaattgga aagagttttg aactttccac aatccaactt gtgtttgaag     540
agagaaaagc aagatgagtc ctgttccttg acccaagctc ttccatctga attgaaggtt     600
tctgctgata cgtttctttt gactggtgct gtttctttgg cttctatgtt gactgaaatt     660
ttcttgttgc agcaggctca aggtatgcca gaaccaggtt ggggtagaat tactgattct     720
catcaatgga cactttgtt gtctttgcat aacgctcaat ttgacttgtt gcaaagaact     780
ccagaagttg ctagatctag agctactcca ttgttggatt tgattaagac tgctttgact     840
ccacatccac cacaaaagca ggcttacggt gttactttgc caacttctgt tttgtttatt     900
gccggtcatg ataccaactt ggctaacttg ggtggtgctt tggaattgaa ctggactttg     960
ccaggtcaac cagataacac tccaccaggt ggtgaattgg tttttgaaag atggagaaga    1020
ttgtccgata ctctcaatg gattcaagtt tctttggtct ttcagacctt gcagcaaatg    1080
agagataaga ctccattgtc tttgaacact ccaccaggtg aagttaagtt gactttggct    1140
ggttgtgaag aaagaaacgc tcaaggtatg tgttctttgg ctggttttac tcaaattgtc    1200
aacgaggcta gaatcccagc ttgttctttg                                      1230
```

```
<210> SEQ ID NO 9
<211> LENGTH: 410
<212> TYPE: PRT
<213> ORGANISM: Artificial Sequence
<220> FEATURE:
<223> OTHER INFORMATION: Phytase mutant

<400> SEQUENCE: 9

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
            130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Trp Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365
```

```
Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 10
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 10
caatctgaac cagaattgaa gttggaatct gttgttattg tttcccgtca cggtgttaga      60
gccccaacta aggctactca attgatgcaa gatgttactc cagatgcttg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat tgtttaaccc attgaagact ggtgtttgtc aattggatgt tgctaacgtt     420
actagagcta ttttggaaag agctggtggt tctattgctg attttactgg tcattaccaa     480
accgcctttc gtgaattgga aagagttttg aactttccac aatccaactt gtgtttgaag     540
agagaaaagc aagatgagtc ctgttccttg acccaagctc ttccatctga attgaaggtt     600
tctgctgata cgtttctttt gactggtgct tggtctttgg cttctatgtt gactgaaatt     660
ttcttgttgc agcaggctca aggtatgcca gaaccaggtt ggggtagaat tactgattct     720
catcaatgga cacttgtt gtctttgcat aacgctcaat ttgacttgtt gcaaagaact     780
ccagaagttg ctagatctag agctactcca ttgttggatt tgattaagac tgctttgact     840
ccacatccac cacaaaagca ggcttacggt gttactttgc caacttctgt tttgtttatt     900
gccggtcatg ataccaactt ggctaacttg ggtggtgctt ggaattgaa ctggactttg     960 ccaggtcaac cagataacac tccaccaggt ggtgaattgg ttttgaaag atggagaaga    1020 ttgtccgata actctcaatg gattcaagtt tctttggtct ttcagacctt gcagcaaatg    1080
agagataaga ctccattgtc tttgaacact ccaccaggtg aagttaagtt gactttggct    1140
ggttgtgaag aaagaaacgc tcaaggtatg tgttctttgg ctggttttac tcaaattgtc    1200
aacgaggcta gaatcccagc ttgttctttg                                     1230
```

```
<210> SEQ ID NO 11
<211> LENGTH: 410
<212> TYPE: PRT
<213> ORGANISM: Artificial Sequence
<220> FEATURE:
<223> OTHER INFORMATION: Phytase mutant

<400> SEQUENCE: 11

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
        35                  40                  45
```

-continued

```
Pro Arg Gly Gly Glu Leu Ile Ala Tyr Leu Gly His Tyr Trp Arg Gln
    50                  55              60

Arg Leu Val Ala Asp Glu Leu Leu Pro Lys Lys Gly Cys Pro Gln Ser
65                  70              75                  80

Gly Gln Val Ala Ile Ile Ala Asp Val Asp Glu Arg Thr Arg Lys Thr
                85              90                  95

Gly Glu Ala Phe Ala Ala Gly Leu Ala Pro Asp Cys Ala Ile Thr Val
                100             105             110

His His Gln Ala Asp Thr Ser Ser Pro Asp Pro Leu Phe Asn Pro Leu
        115             120             125

Lys Thr Gly Val Cys Gln Leu Asp Val Ala Asn Val Thr Arg Ala Ile
    130             135             140

Leu Glu Arg Ala Gly Gly Ser Ile Ala Asp Phe Thr Gly His Tyr Gln
145             150             155             160

Thr Ala Phe Arg Glu Leu Glu Arg Val Leu Asn Phe Pro Gln Ser Asn
            165             170             175

Leu Cys Leu Lys Arg Glu Lys Gln Asp Glu Ser Cys Ser Leu Thr Gln
            180             185             190

Ala Leu Pro Ser Glu Leu Lys Val Ser Ala Asp Asn Val Ser Leu Thr
            195             200             205

Gly Ala Val Ser Leu Ala Ser Met Leu Thr Glu Ile Phe Leu Leu Gln
    210             215             220

Gln Ala Gln Gly Met Pro Glu Pro Gly Trp Gly Arg Ile Thr Asp Ser
225             230             235             240

His Gln Trp Asn Thr Leu Leu Ser Leu His Asn Ala Tyr Phe Asp Leu
            245             250             255

Leu Gln Arg Thr Pro Glu Val Ala Arg Ser Arg Ala Thr Pro Leu Leu
            260             265             270

Asp Leu Ile Lys Thr Ala Leu Thr Pro His Pro Pro Gln Lys Gln Ala
    275             280             285

Tyr Gly Val Thr Leu Pro Thr Ser Val Leu Phe Ile Ala Gly His Asp
    290             295             300

Thr Asn Leu Ala Asn Leu Gly Gly Ala Leu Glu Leu Asn Trp Thr Leu
305             310             315             320

Pro Gly Gln Pro Asp Asn Thr Pro Pro Gly Gly Glu Leu Val Phe Glu
            325             330             335

Arg Trp Arg Arg Leu Ser Asp Asn Ser Gln Trp Ile Gln Val Ser Leu
            340             345             350

Val Phe Gln Thr Leu Gln Gln Met Arg Asp Lys Thr Pro Leu Ser Leu
            355             360             365

Asn Thr Pro Pro Gly Glu Val Lys Leu Thr Leu Ala Gly Cys Glu Glu
    370             375             380

Arg Asn Ala Gln Gly Met Cys Ser Leu Ala Gly Phe Thr Gln Ile Val
385             390             395             400

Asn Glu Ala Arg Ile Pro Ala Cys Ser Leu
            405             410
```

<210> SEQ ID NO 12
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 12

```
caatctgaac cagaattgaa gttggaatct gttgttattg tttcccgtca cggtgttaga      60
gccccaacta aggctactca attgatgcaa gatgttactc cagatgcttg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat gtttaaccc attgaagact ggtgtttgtc aattggatgt tgctaacgtt     420
actagagcta ttttggaaag agctggtggt tctattgctg attttactgg tcattaccaa     480 accgccttttc gtgaattgga aagagttttg aactttccac aatccaactt gtgtttgaag     540
agagaaaagc aagatgagtc ctgttccttg acccaagctc ttccatctga attgaaggtt     600
tctgctgata acgtttcttt gactggtgct gtttctttgg cttctatgtt gactgaaatt     660
ttcttgttgc agcaggctca aggtatgcca gaaccaggtt ggggtagaat tactgattct     720
catcaatgga acactttgtt gtctttgcat aacgcttact ttgacttgtt gcaaagaact     780
ccagaagttg ctagatctag agctactcca ttgttggatt tgattaagac tgctttgact     840
ccacatccac cacaaaagca ggcttacggt gttactttgc caacttctgt tttgttattt     900
gccggtcatg ataccaactt ggctaacttg ggtggtgctt tggaattgaa ctggactttg     960
ccaggtcaac agataacac tccaccaggt ggtgaattgg tttttgaaag atggagaaga    1020
ttgtccgata actctcaatg gattcaagtt tctttggtct ttcagacctt gcagcaaatg    1080
agagataaga ctccattgtc tttgaacact ccaccaggtg aagttaagtt gactttggct    1140
ggttgtgaag aaagaaacgc tcaaggtatg tgttctttgg ctggttttac tcaaattgtc    1200
aacgaggcta gaatcccagc ttgttctttg                                     1230

<210> SEQ ID NO 13
<211> LENGTH: 410
<212> TYPE: PRT
<213> ORGANISM: Artificial Sequence
<220> FEATURE:
<223> OTHER INFORMATION: Phytase mutant

<400> SEQUENCE: 13

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140
```

```
Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Glu Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

<210> SEQ ID NO 14
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 14
caatctgaac cagaattgaa gttggaatct gttgttattg tttcccgtca cggtgttaga        60
gccccaacta aggctactca attgatgcaa gatgttactc cagatgcttg gccaacttgg       120
ccagttaagt tgggtgaatt gactccaaga ggtggtgaat tgattgctta cttgggtcat       180
tactggagac aaagattggt tgctgatgaa ttgttgccaa agaagggttg tccacaatct       240
ggtcaagttg ctattattgc tgatgttgat gaacgcacta gaaagaccgg tgaggctttt       300
gctgctggtt tggctccaga ttgtgctatt actgttcatc atcaagctga tacttcttcc       360
ccagatccat gttttaaccc attgaagact ggtgtttgtc aattggatgt tgctaacgtt       420
actagagcta tttttggaaag agctggtggt tctattgctg attttactgg tcattaccaa       480
accgcctttc gtgaattgga aagagttttg aactttccac aatccaactt gtgtttgaag       540

-continued

```
agagaaaagc aagatgagtc ctgttccttg acccaagctc ttccatctga attgaaggtt    600
tctgctgata acgtttcttt gactggtgct gtttctttgg cttctatgtt gactgaaatt    660
ttcttgttgc agcaggctca aggtatgcca gaaccaggtt ggggtagaat tactgattct    720
catcaatgga acactttgtt gtctttgcat aacgctcaat ttgacttgtt ggagagaact    780
ccagaagttg ctagatctag agctactcca ttgttggatt tgattaagac tgctttgact    840
ccacatccac cacaaaagca ggcttacggt gttactttgc caacttctgt tttgtttatt    900
gccggtcatg ataccaactt ggctaacttg ggtggtgctt tggaattgaa ctggactttg    960
ccaggtcaac cagataacac tccaccaggt ggtgaattgg tttttgaaag atggagaaga   1020
ttgtccgata actctcaatg gattcaagtt tctttggtct ttcagacctt gcagcaaatg   1080
agagataaga ctccattgtc tttgaacact ccaccaggtg aagttaagtt gactttggct   1140
ggttgtgaag aaagaaacgc tcaaggtatg tgttctttgg ctggttttac tcaaattgtc   1200
aacgaggcta gaatcccagc ttgttctttg                                    1230
```

<210> SEQ ID NO 15
<211> LENGTH: 410
<212> TYPE: PRT
<213> ORGANISM: Artificial Sequence
<220> FEATURE:
<223> OTHER INFORMATION: Phytase mutant

<400> SEQUENCE: 15

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240
```

```
His Gln Trp Asn Thr Leu Leu Ser Leu His Asn Ala Gln Phe Asp Leu
            245                 250                 255

Leu Gln Arg Thr Pro Glu Val Ala Arg Pro Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 16
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 16
caatctgaac cagaattgaa gttggaatct gttgttattg tttcccgtca cggtgttaga      60
gccccaacta aggctactca attgatgcaa gatgttactc cagatgcttg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat gtttaaccc attgaagact ggtgtttgtc aattggatgt tgctaacgtt     420
actagagcta ttttggaaag agctggtggt tctattgctg attttactgg tcattaccaa     480
accgcctttc gtgaattgga aagagttttg aactttccac aatccaactt gtgtttgaag     540
agagaaaagc aagatgagtc ctgttccttg acccaagctc ttccatctga attgaaggtt     600
tctgctgata cgtttctttt gactggtgct gtttctttgg cttctatgtt gactgaaatt     660
ttcttgttgc agcaggctca aggtatgcca gaaccaggtt ggggtagaat tactgattct     720
catcaatgga acactttgtt gtctttgcat aacgctcaat tgacttgtt gcaaagaact     780 ccagaagttg ctagaccaag agctactcca ttgttggatt tgattaagac tgctttgact     840
ccacatccac cacaaaagca ggcttacggt gttactttgc caacttctgt tttgtttatt     900
gccggtcatg ataccaactt ggctaacttg ggtggtgctt tggaattgaa ctggactttg     960
ccaggtcaac cagataacac tccaccaggt ggtgaattgg tttttgaaag atggagaaga    1020
ttgtccgata actctcaatg gattcaagtt tctttggtct ttcagacctt gcagcaaatg    1080
```

-continued

```
agagataaga ctccattgtc tttgaacact ccaccaggtg aagttaagtt gactttggct     1140
ggttgtgaag aaagaaacgc tcaaggtatg tgttctttgg ctggttttac tcaaattgtc     1200
aacgaggcta gaatcccagc ttgttctttg                                       1230
```

<210> SEQ ID NO 17
<211> LENGTH: 410
<212> TYPE: PRT
<213> ORGANISM: Artificial Sequence
<220> FEATURE:
<223> OTHER INFORMATION: Phytase mutant

<400> SEQUENCE: 17

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Pro Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335
```

-continued

```
Arg Trp Arg Arg Leu Ser Asp Asn Ser Gln Trp Ile Gln Val Ser Leu
        340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 18
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 18
caatctgaac cagaattgaa gttggaatct gttgttattg tttcccgtca cggtgttaga      60
gccccaacta aggctactca attgatgcaa gatgttactc cagatccatg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat gttttaaccc attgaagact ggtgtttgtc aattggatgt tgctaacgtt     420
actagagcta tttttggaaag agctggtggt tctattgctg atttttactgg tcattaccaa     480 accgcctttc gtgaattgga aagagttttg aactttccac aatccaactt gtgtttgaag     540
agagaaaagc aagatgagtc ctgttccttg acccaagctc ttccatctga attgaaggtt     600
tctgctgata acgtttcttt gactggtgct tggtctttgg cttctatgtt gactgaaatt     660
ttcttgttgc agcaggctca aggtatgcca gaaccaggtt ggggtagaat tactgattct     720
catcaatgga acactttgtt gtctttgcat aacgctcaat ttgacttgtt gcaaagaact     780
ccagaagttg ctagatctag agctactcca ttgttggatt tgattaagac tgcttttgact     840 ccacatccac cacaaaagca ggcttacggt gttactttgc caacttctgt tttgtttatt     900
gccggtcatg ataccaactt ggctaacttg ggtggtgctt tggaattgaa ctggactttg     960
ccaggtcaac cagataacac tccaccaggt ggtgaattgg ttttttgaaag atggagaaga    1020 ttgtccgata actctcaatg gattcaagtt tctttggtct ttcagacctt gcagcaaatg    1080
agagataaga ctccattgtc tttgaacact ccaccaggtg aagttaagtt gactttggct    1140
ggttgtgaag aaagaaacgc tcaaggtatg tgttctttgg ctggttttac tcaaattgtc    1200
aacgaggcta gaatcccagc ttgttctttg                                       1230
```

```
<210> SEQ ID NO 19
<211> LENGTH: 410
<212> TYPE: PRT
<213> ORGANISM: Artificial Sequence
<220> FEATURE:
<223> OTHER INFORMATION: Phytase mutant

<400> SEQUENCE: 19

Gln Ser Glu Pro Glu Leu Lys Leu Glu Ser Val Val Ile Val Ser Arg
```

```
1                5                10               15
His Gly Val Arg Ala Pro Thr Lys Ala Thr Gln Leu Met Gln Asp Val
            20               25               30

Thr Pro Asp Pro Trp Pro Thr Trp Pro Val Lys Leu Gly Glu Leu Thr
            35               40               45

Pro Arg Gly Gly Glu Leu Ile Ala Tyr Leu Gly His Tyr Trp Arg Gln
  50               55               60

Arg Leu Val Ala Asp Glu Leu Leu Pro Lys Lys Gly Cys Pro Gln Ser
65               70               75               80

Gly Gln Val Ala Ile Ile Ala Asp Val Asp Glu Arg Thr Arg Lys Thr
            85               90               95

Gly Glu Ala Phe Ala Ala Gly Leu Ala Pro Asp Cys Ala Ile Thr Val
            100              105              110

His His Gln Ala Asp Thr Ser Ser Pro Asp Pro Leu Phe Asn Pro Leu
            115              120              125

Lys Thr Gly Val Cys Gln Leu Asp Val Ala Asn Val Thr Arg Ala Ile
  130              135              140

Leu Glu Arg Ala Gly Gly Ser Ile Ala Asp Phe Thr Gly His Tyr Gln
145              150              155              160

Thr Ala Phe Arg Glu Leu Glu Arg Val Leu Asn Phe Pro Gln Ser Asn
            165              170              175

Leu Cys Leu Lys Arg Glu Lys Gln Asp Glu Ser Cys Ser Leu Thr Gln
            180              185              190

Ala Leu Pro Ser Glu Leu Lys Val Ser Ala Asp Asn Val Ser Leu Thr
            195              200              205

Gly Ala Val Ser Leu Ala Ser Met Leu Thr Glu Ile Phe Leu Leu Gln
  210              215              220

Gln Ala Gln Gly Met Pro Glu Pro Gly Trp Gly Arg Ile Thr Asp Ser
225              230              235              240

His Gln Trp Asn Thr Leu Leu Ser Leu His Asn Ala Tyr Phe Asp Leu
            245              250              255

Leu Gln Arg Thr Pro Glu Val Ala Arg Ser Arg Ala Thr Pro Leu Leu
            260              265              270

Asp Leu Ile Lys Thr Ala Leu Thr Pro His Pro Pro Gln Lys Gln Ala
            275              280              285

Tyr Gly Val Thr Leu Pro Thr Ser Val Leu Phe Ile Ala Gly His Asp
  290              295              300

Thr Asn Leu Ala Asn Leu Gly Gly Ala Leu Glu Leu Asn Trp Thr Leu
305              310              315              320

Pro Gly Gln Pro Asp Asn Thr Pro Pro Gly Gly Glu Leu Val Phe Glu
            325              330              335

Arg Trp Arg Arg Leu Ser Asp Asn Ser Gln Trp Ile Gln Val Ser Leu
            340              345              350

Val Phe Gln Thr Leu Gln Gln Met Arg Asp Lys Thr Pro Leu Ser Leu
            355              360              365

Asn Thr Pro Pro Gly Glu Val Lys Leu Thr Leu Ala Gly Cys Glu Glu
  370              375              380

Arg Asn Ala Gln Gly Met Cys Ser Leu Ala Gly Phe Thr Gln Ile Val
385              390              395              400

Asn Glu Ala Arg Ile Pro Ala Cys Ser Leu
            405              410
```

<210> SEQ ID NO 20

```
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 20
caatctgaac cagaattgaa gttggaatct gttgttattg tttcccgtca cggtgttaga        60
gccccaacta aggctactca attgatgcaa gatgttactc cagatccatg gccaacttgg       120
ccagttaagt tgggtgaatt gactccaaga ggtggtgaat tgattgctta cttgggtcat       180
tactggagac aaagattggt tgctgatgaa ttgttgccaa agaagggttg tccacaatct       240
ggtcaagttg ctattattgc tgatgttgat gaacgcacta gaaagaccgg tgaggctttt       300
gctgctggtt tggctccaga ttgtgctatt actgttcatc atcaagctga tacttcttcc       360
ccagatccat tgtttaaccc attgaagact ggtgtttgtc aattggatgt tgctaacgtt       420
actagagcta ttttggaaag agctggtggt tctattgctg attttactgg tcattaccaa       480 accgccttc gtgaattgga aagagtttttg aactttccac aatccaactt gtgtttgaag       540
agagaaaagc aagatgagtc ctgttccttg acccaagctc ttccatctga attgaaggtt       600
tctgctgata acgtttcttt gactggtgct gtttctttgg cttctatgtt gactgaaatt       660
ttcttgttgc agcaggctca aggtatgcca gaaccaggtt ggggtagaat tactgattct       720
catcaatgga cactttgtt gtctttgcat aacgcttact ttgacttgtt gcaaagaact       780
ccagaagttg ctagatctag agctactcca ttgttggatt tgattaagac tgctttgact       840
ccacatccac cacaaaagca ggcttacggt gttactttgc caacttctgt tttgtttatt       900
gccggtcatg ataccaactt ggctaacttg ggtggtgctt tggaattgaa ctggactttg       960
ccaggtcaac cagataacac tccaccaggt ggtgaattgg ttttttgaaag atggagaaga      1020 ttgtccgata actctcaatg gattcaagtt tctttggtct ttcagacctt gcagcaaatg      1080
agagataaga ctccattgtc tttgaacact ccaccaggtg aagttaagtt gactttggct      1140
ggttgtgaag aaagaaacgc tcaaggtatg tgttctttgg ctggttttac tcaaattgtc      1200
aacgaggcta gaatcccagc ttgttctttg                                        1230
```

```
<210> SEQ ID NO 21
<211> LENGTH: 410
<212> TYPE: PRT
<213> ORGANISM: Artificial Sequence
<220> FEATURE:
<223> OTHER INFORMATION: Phytase mutant

<400> SEQUENCE: 21

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
```

-continued

```
              100             105              110
His His Gln Ala Asp Thr Ser Ser Pro Asp Pro Leu Phe Asn Pro Leu
         115              120              125

Lys Thr Gly Val Cys Gln Leu Asp Val Ala Asn Val Thr Arg Ala Ile
     130              135              140

Leu Glu Arg Ala Gly Gly Ser Ile Ala Asp Phe Thr Gly His Tyr Gln
145              150              155              160

Thr Ala Phe Arg Glu Leu Glu Arg Val Leu Asn Phe Pro Gln Ser Asn
              165              170              175

Leu Cys Leu Lys Arg Glu Lys Gln Asp Glu Ser Cys Ser Leu Thr Gln
         180              185              190

Ala Leu Pro Ser Glu Leu Lys Val Ser Ala Asp Asn Val Ser Leu Thr
         195              200              205

Gly Ala Trp Ser Leu Ala Ser Met Leu Thr Glu Ile Phe Leu Leu Gln
         210              215              220

Gln Ala Gln Gly Met Pro Glu Pro Gly Trp Gly Arg Ile Thr Asp Ser
225              230              235              240

His Gln Trp Asn Thr Leu Leu Ser Leu His Asn Ala Tyr Phe Asp Leu
              245              250              255

Leu Gln Arg Thr Pro Glu Val Ala Arg Ser Arg Ala Thr Pro Leu Leu
              260              265              270

Asp Leu Ile Lys Thr Ala Leu Thr Pro His Pro Gln Lys Gln Ala
         275              280              285

Tyr Gly Val Thr Leu Pro Thr Ser Val Leu Phe Ile Ala Gly His Asp
     290              295              300

Thr Asn Leu Ala Asn Leu Gly Gly Ala Leu Glu Leu Asn Trp Thr Leu
305              310              315              320

Pro Gly Gln Pro Asp Asn Thr Pro Pro Gly Gly Glu Leu Val Phe Glu
              325              330              335

Arg Trp Arg Arg Leu Ser Asp Asn Ser Gln Trp Ile Gln Val Ser Leu
         340              345              350

Val Phe Gln Thr Leu Gln Gln Met Arg Asp Lys Thr Pro Leu Ser Leu
         355              360              365

Asn Thr Pro Pro Gly Glu Val Lys Leu Thr Leu Ala Gly Cys Glu Glu
     370              375              380

Arg Asn Ala Gln Gly Met Cys Ser Leu Ala Gly Phe Thr Gln Ile Val
385              390              395              400

Asn Glu Ala Arg Ile Pro Ala Cys Ser Leu
              405              410
```

```
<210> SEQ ID NO 22
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 22
caatctgaac cagaattgaa gttggaatct gttgttattg tttcccgtca cggtgttaga      60
gccccaacta aggctactca attgatgcaa gatgttactc cagatgcttg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
```

-continued

```
gctgctggtt tggctccaga ttgtgctatt actgttcatc atcaagctga tacttcttcc        360
ccagatccat tgtttaaccc attgaagact ggtgtttgtc aattggatgt tgctaacgtt        420
actagagcta ttttggaaag agctggtggt tctattgctg attttactgg tcattaccaa        480 accgccttc gtgaattgga aagagttttg aactttccac aatccaactt gtgtttgaag         540
agagaaaagc aagatgagtc ctgttccttg acccaagctc ttccatctga attgaaggtt        600
tctgctgata cgtttctttt gactggtgct tggtctttgg cttctatgtt gactgaaatt        660
ttcttgttgc agcaggctca aggtatgcca gaaccaggtt ggggtagaat tactgattct        720
catcaatgga acactttgtt gtctttgcat aacgcttact ttgacttgtt gcaaagaact        780
ccagaagttg ctagatctag agctactcca ttgttggatt tgattaagac tgctttgact        840
ccacatccac cacaaaagca ggcttacggt gttactttgc caacttctgt tttgtttatt        900
gccggtcatg ataccaactt ggctaacttg ggtggtgctt tggaattgaa ctggactttg        960
ccaggtcaac cagataacac tccaccaggt ggtgaattgg tttttgaaag atggagaaga        1020
ttgtccgata actctcaatg gattcaagtt tctttggtct ttcagacctt gcagcaaatg        1080
agagataaga ctccattgtc tttgaacact ccaccaggtg aagttaagtt gactttggct        1140
ggttgtgaag aaagaaacgc tcaaggtatg tgttctttgg ctggtttac  tcaaattgtc        1200 aacgaggcta gaatcccagc ttgttctttg                                        1230
```

<210> SEQ ID NO 23
<211> LENGTH: 410
<212> TYPE: PRT
<213> ORGANISM: Artificial Sequence
<220> FEATURE:
<223> OTHER INFORMATION: Phytase mutant

<400> SEQUENCE: 23

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Pro Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
```

```
            195                 200                 205
Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

<210> SEQ ID NO 24
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 24

```
caatctgaac cagaattgaa gttggaatct gttgttattg tttcccgtca cggtgttaga      60
gccccaacta aggctactca attgatgcaa gatgttactc cagatccatg gccaacttgg     120
ccagttaagt tgggtgaatt gactccaaga ggtggtgaat tgattgctta cttgggtcat     180
tactggagac aaagattggt tgctgatgaa ttgttgccaa agaagggttg tccacaatct     240
ggtcaagttg ctattattgc tgatgttgat gaacgcacta gaaagaccgg tgaggctttt     300
gctgctggtt tggctccaga ttgtgctatt actgttcatc atcaagctga tacttcttcc     360
ccagatccat gtgtttaccc attgaagact ggtgtttgtc aattggatgt tgctaacgtt     420
actagagcta ttttggaaag agctggtggt tctattgctg attttactgg tcattaccaa     480 accgccttttc gtgaattgga aagagttttg aactttccac aatccaactt gtgtttgaag     540
agagaaaagc aagatgagtc ctgttccttg acccaagctc ttccatctga attgaaggtt     600
tctgctgata acgtttcttt gactggtgct ggtctttggg cttctatgtt gactgaaatt     660
ttcttgttgc agcaggctca aggtatgcca gaaccaggtt ggggtagaat tactgattct     720
catcaatgga acactttgtt gtctttgcat aacgcttact ttgacttgtt gcaaagaact     780
ccagaagttg ctagatctag agctactcca ttgttggatt tgattaagac tgctttgact     840
```

```
ccacatccac cacaaaagca ggcttacggt gttactttgc caacttctgt tttgtttatt      900
gccggtcatg ataccaactt ggctaacttg ggtggtgctt tggaattgaa ctggactttg      960
ccaggtcaac cagataacac tccaccaggt ggtgaattgg tttttgaaag atggagaaga     1020
ttgtccgata actctcaatg gattcaagtt tctttggtct ttcagacctt gcagcaaatg     1080
agagataaga ctccattgtc tttgaacact ccaccaggtg aagttaagtt gactttggct     1140
ggttgtgaag aaagaaacgc tcaaggtatg tgttctttgg ctggttttac tcaaattgtc     1200
aacgaggcta gaatcccagc ttgttctttg                                      1230
```

```
<210> SEQ ID NO 25
<211> LENGTH: 410
<212> TYPE: PRT
<213> ORGANISM: Artificial Sequence
<220> FEATURE:
<223> OTHER INFORMATION: Phytase mutant

<400> SEQUENCE: 25

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Pro Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Glu Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Trp Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
```

```
        290              295              300

Thr Asn Leu Ala Asn Leu Gly Gly Ala Leu Glu Leu Asn Trp Thr Leu
305              310              315              320

Pro Gly Gln Pro Asp Asn Thr Pro Pro Gly Gly Glu Leu Val Phe Glu
            325              330              335

Arg Trp Arg Arg Leu Ser Asp Asn Ser Gln Trp Ile Gln Val Ser Leu
            340              345              350

Val Phe Gln Thr Leu Gln Gln Met Arg Asp Lys Thr Pro Leu Ser Leu
        355              360              365

Asn Thr Pro Pro Gly Glu Val Lys Leu Thr Leu Ala Gly Cys Glu Glu
        370              375              380

Arg Asn Ala Gln Gly Met Cys Ser Leu Ala Gly Phe Thr Gln Ile Val
385              390              395              400

Asn Glu Ala Arg Ile Pro Ala Cys Ser Leu
            405              410
```

<210> SEQ ID NO 26
<211> LENGTH: 1230
<212> TYPE: DNA
<213> ORGANISM: Artificial Sequence
<220> FEATURE:
<223> OTHER INFORMATION: Nucleotide sequence encoding phytase mutant

<400> SEQUENCE: 26

```
caatctgaac cagaattgaa gttggaatct gttgttattg tttcccgtca cggtgttaga        60
gccccaacta aggctactca attgatgcaa gatgttactc cagatccatg gccaacttgg       120
ccagttaagt tgggtgaatt gactccaaga ggtggtgaat tgattgctta cttgggtcat       180
tactggagac aaagattggt tgctgatgaa ttgttgccaa agaagggttg tccacaatct       240
ggtcaagttg ctattattgc tgatgttgat gaacgcacta gaaagaccgg tgaggctttt       300
gctgctggtt tggctccaga ttgtgctatt actgttcatc atcaagctga tacttcttcc       360
ccagatccat gttttgagcc attgaagact ggtgtttgtc aattggatgt tgctaacgtt       420
actagagcta ttttggaaag agctggtggt tctattgctg attttactgg tcattaccaa       480 accgccttc gtgaattgga aagagttttg aactttccac aatccaactt gtgtttgaag       540
agagaaaagc aagatgagtc ctgttccttg acccaagctc ttccatctga attgaaggtt       600
tctgctgata acgtttcttt gactggtgct tggtctttgg cttctatgtt gactgaaatt       660
ttcttgttgc agcaggctca aggtatgcca gaaccaggtt ggggtagaat tactgattct       720
catcaatgga cactttgtt gtctttgcat aacgcttact ttgacttgtt gcaaagaact       780
ccagaagttg ctagatctag agctactcca ttgttggatt tgattaagac tgctttgact       840
ccacatccac cacaaaagca ggcttacggt gttactttgc caacttctgt tttgtttatt       900
gccggtcatg ataccaactt ggctaacttg ggtggtgctt tggaattgaa ctggactttg       960
ccaggtcaac cagataacac tccaccaggt ggtgaattgg tttttgaaag atggagaaga      1020
ttgtccgata actctcaatg gattcaagtt tctttggtct ttcagacctt gcagcaaatg      1080
agagataaga ctccattgtc tttgaacact ccaccaggtg aagttaagtt gactttggct      1140
ggttgtgaag aaagaaacgc tcaaggtatg tgttctttgg ctggttttac tcaaattgtc      1200
aacgaggcta gaatcccagc ttgttctttg                                      1230
```

<210> SEQ ID NO 27
<211> LENGTH: 32
<212> TYPE: DNA

-continued

```
<213> ORGANISM: Artificial Sequence
<220> FEATURE:
<223> OTHER INFORMATION: M0-F1 primer

<400> SEQUENCE: 27
ggcgaattcc agtcagaacc agagttgaag tt                              32

<210> SEQ ID NO 28
<211> LENGTH: 32
<212> TYPE: DNA
<213> ORGANISM: Artificial Sequence
<220> FEATURE:
<223> OTHER INFORMATION: M0-R1 primer

<400> SEQUENCE: 28
atagcggccg cttacaagga acaagcaggg at                             32
```

PHYTASE MUTANT

CROSS REFERENCE TO RELATED APPLICATIONS

This application is the national phase of International Application No. PCT/CN2021/094767 titled "PHYTASE MUTANT", which claims the priority of Chinese patent application No. 202010442538.3, filed with the China National Intellectual Property Administration on May 22, 2020 and titled with "PHYTASE MUTANT", and Chinese Patent Application No. 202011596375.0, filed with the China National Intellectual Property Administration on Dec. 29, 2020 and titled with "PHYTASE MUTANT", which are hereby incorporated by reference in entirety.

INCORPORATION OF SEQUENCE LISTING

This application contains references to amino acid sequences and/or nucleic acid sequences which have been submitted concurrently herewith as the sequence listing text file entitled "220080-APXU-VLAND-Sequence-Listing ST25.txt", file size 70,474 bytes, created on Nov. 18, 2022. The aforementioned sequence listing is hereby incorporated by reference in its entirety pursuant to 37 C.F.R. $1.52 (e) (5).

FIELD

The present disclosure relates to the field of biotechnology, and in particular to a phytase mutant, a preparation method and an application thereof, a DNA molecule encoding the phytase mutant, a vector and a host cell.

BACKGROUND

Phytase is a phosphatase that hydrolyzes phytic acid. It degrades phytate phosphorus (inositol hexaphosphate) into inositol and inorganic phosphoric acid. This enzyme is divided into two categories: 3-phytase (EC. 3.1.3.8) and 6-phytase (EC. 3.1.2.6). Phytase is widely found in plants, animals and microorganisms, for example, higher plants such as corn and wheat, prokaryotic microorganisms such as *Bacillus subtilis, Pseudomonas, Lactobacillus* and *Escherichia coli*, and eukaryotic microorganisms such as yeast, *Rhizopus*, and *Aspergillus*.

In the seeds of crops such as grains, beans and oilseeds, the basic storage form of phosphorus is phytate phosphorus, the content of which is as high as 1% to 3%, accounting for 60% to 80% of the total phosphorus in plants. However, phosphorus in the form of phytate phosphorus is difficult to be utilized due to the lack of enzymes that can decompose phytic acid in monogastric animals, and its utilization rate is only 0% to 40%, which causes many problems: firstly, it is the origin of the waste of phosphorus source. On the one hand, the phosphorus source in the feed cannot be effectively utilized; on the other hand, in order to meet the needs of animals for phosphorus, inorganic phosphorus must be added to the feed, thus the cost of which increases. Secondly, it results in the formation of high phosphorus feces which pollutes the environment. About 85% of the phytate phosphorus in the feed will be directly excreted by animals, and a large amount of phytate phosphorus in the feces will seriously pollute the water and soil. In addition, phytate phosphorus is also an anti-nutritional factor, which will chelate with a variety of metal ions such as $Zn^{2+}$, $Ca^{2+}$, $Cu^{2+}$ and $Fe^{2+}$ and proteins into corresponding insoluble complexes during the digestion and absorption process in animals' gastrointestinal tract, reducing the efficient utilization of these nutrients by animals.

Phytase can be used as a feed additive for monogastric animals, and the feeding effect thereof has been confirmed worldwide. It can increase the utilization rate of phosphorus in plant feed by 60%, reduce phosphorus excretion in feces by 40%, and reduce the anti-nutritional effect of phytic acid. Therefore, adding phytase to feed is of great significance to improve the production efficiency of livestock and poultry industry, and to reduce the pollution of phytate phosphorus to the environment.

There are mainly two types of phytase in current industrial production: fungal phytase derived from *Aspergillus niger* and bacterial phytase derived from *Escherichia coli*. Among them, the phytase APPA derived from *Escherichia coli* has the characteristics of high specific activity and good stability in digestive tract. At present, the phytase is mainly applied in the feed industry by being added directly to the powder feed or being sprayed on the pellet feed.

There is a short high temperature stage of 80-90° C. in the production process of pellet feed. The thermal stability of bacterial phytase APPA is poor. When the aqueous solution of bacterial phytase is kept at 70° C. for 5 minutes, the residual enzyme activity is less than 30%; when the bacterial phytase is directly added to animal feed for pelletization, the residual enzyme activity is generally less than 20%, which limits the application of phytase APPA in pellet feed. The method of spraying the phytase liquid on the pelletized feed not only increases the equipment investment, but also cannot guarantee the stability and the uniformity of distribution of the phytase preparation in the feed. Therefore, improving the thermal stability of the phytase has important practical significance for the phytase currently used in feed.

SUMMARY

In view of this, the present invention provides a phytase mutant, in which a mutant protein is obtained with improved heat resistance, thereby facilitating the wide application of phytase in the field of feed.

In order to achieve the above-mentioned purpose of the present invention, the present invention provides the following technical solutions:

The present invention relates to a phytase mutant, which comprises an amino acid sequence having at least 90% identity with SEQ ID NO: 3, and comprises an amino acid substitution compared with SEQ ID NO: 3 at at least one position selected from the group consisting of 36, 126, 211, 253, 258, and 266.

In some embodiments of the present invention, the amino acid sequence of the mutant has at least 91%, 92%, 93%, 94%, 95%, 96%, 97%, 98%, or at least 99% identity with SEQ ID NO: 3.

In some more specific embodiments, the amino acid sequence of the mutant has at least 99.1%, 99.2%, 99.3%, 99.4%, 99.5%, 99.6%, 99.7%, 99.8%, or at least 99.9% identity with SEQ ID NO: 3.

In some embodiments of the present invention, the mutant comprises at least one amino acid substitution selected from the group consisting of A36P, N126E, V211W, Q253Y, Q258E, and S266P.

In some embodiments of the present invention, the mutant comprises an amino acid substitution or a combination selected from the group consisting of A36P, N126E, V211W, Q253Y, Q258E, S266P, A36P/V211W, A36P/Q253Y, V211W/Q253Y, A36P/V211W/Q253Y and A36P/N126E/V211W/Q253Y.

The present invention also provides a DNA molecule encoding the above-mentioned phytase mutant.

The present invention also provides a recombinant expression vector comprising the above DNA molecule.

The present invention also provides a host cell comprising the above-mentioned recombinant expression vector.

The heat resistance of the recombinant phytase expressed by transferring the above-mentioned plasmids into host cells is significantly improved.

In some embodiments of the present invention, the host cell is *Pichia pastoris*.

In some embodiments of the present invention, the host cell is *Trichoderma reesei*.

The present invention also provides a method for preparing the above-mentioned phytase mutant, comprising:

Step 1: Obtaining a DNA molecule encoding a phytase mutant, wherein the phytase mutant comprises an amino acid sequence having at least 90% identity with SEQ ID NO: 3, and contains an amino acid substitution compared with SEQ ID NO: 3 at at least one position selected from the group consisting of 36, 126, 211, 253, 258, and 266;

Step 2: Linking the DNA molecule obtained in step 1 with an expression vector to construct a recombinant expression vector and transforming the vector into a host cell;

Step 3: Inducing the host cell containing the recombinant expression vector to express a mutant protein, and separating and purifying the expressed mutant protein.

In some embodiments of the present invention, the phytase mutant described in step 1 comprises at least one amino acid substitution selected from the group consisting of A36P, N126E, V211W, Q253Y, Q258E, and S266P.

In some embodiments of the present invention, the host cell described in step 2 is *Pichia pastoris*.

In some embodiments of the present invention, the host cell described in step 2 is *Trichoderma reesei*.

The present invention also provides a use of the above-mentioned phytase mutant in feed.

Based on phytase APPA-M0, the present invention provides a phytase mutant comprising at least one mutation site of A36P, N126E, V211W, Q253Y, Q258E and S266P. Compared with APPA-M0, after the mutants were treated at 80° C. for 5 min, the residual enzyme activity rate thereof was generally increased by 8.9%-121.2%, indicating a significantly improved heat resistance. Among them, after the mutants PHY-M2, PHY-M3, PHY-M7, PHY-M9, PHY-M10 and PHY-M11 were treated at 85° C. for 5 min, the residual enzyme activity rate thereof could still reach 50.98-74.60%, which was still higher than that of APPA-M0 by 17.2%-71.5%, indicating a better heat resistance. The mutants provided by the present invention have significantly improved heat resistance, which is beneficial to the wide application of phytase in feed.

DETAILED DESCRIPTION

The present invention discloses a phytase mutant, a preparation method and an application thereof, a DNA molecule encoding the phytase mutant, a vector, and a host cell. Those skilled in the art can learn from the content of this document and achieve the present invention by appropriately improving the process parameters. The method and application of the present invention have been described through the preferred embodiments, and it is obvious that the method and application described herein may be changed or appropriately modified and combined without departing from the content, spirit and scope of the present invention to achieve and apply the technology of the present invention.

In the present invention, the nomenclature for defining amino acid positions is based on the amino acid sequence of the phytase from *Escherichia coli* deposited in Genbank under the accession number ABF60232, which is provided in the Sequence Listing as SEQ ID NO: 1 (amino acids 1-410). Thus, in this context, the base SEQ ID NO: 1 for position numbering starts at Q1 (Gln1) and ends at L410 (Leu410). SEQ ID NO: 1 serves as the standard for position numbering and thus serves as the basis for the nomenclature.

In the present invention, conventional techniques and methods used in the fields of genetic engineering and molecular biology are employed, such as the methods described in MOLECULAR CLONING: A LABORATORY MANUAL, 3nd Ed. (Sambrook, 2001) and CURRENT PROTOCOLS IN MOLECULAR BIOLOGY (Ausubel, 2003). These general references provide definitions and methods known to those skilled in the art. However, those skilled in the art can use other conventional methods, experimental schemes and reagents in the art on the basis of the technical solutions described in the present invention, which are not limited to the specific embodiments of the present invention. For example, in the present invention, the following experimental materials and reagents could be used:

Strains and vectors: *Escherichia coli* DH5α, *Pichia pastoris* GS115, vector pPIC9k, Amp, and G418 were purchased from Invitrogen.

Enzymes and kits: PCR enzyme and ligase were purchased from Takara, restriction enzyme were purchased from Fermentas, plasmid extraction kit and gel purification recovery kit were purchased from Omega, GeneMorph II random mutagenesis kit was purchased from Beijing Biomars-technology Co., Ltd.

Medium Formulas:

*Escherichia coli* medium (LB medium): 0.5% yeast extract, 1% peptone, 1% NaCl, pH 7.0;

Yeast medium (YPD medium): 1% yeast extract, 2% peptone, 2% glucose;

Yeast screening medium (MD medium): 2% peptone, 2% agarose;

BMGY medium: 2% peptone, 1% yeast extract, 100 mM potassium phosphate buffer (pH 6.0), 1.34% YNB, $4 \times 10^{-5}\%$ biotin, 1% glycerol;

BMMY medium: 2% peptone, 1% yeast extract, 100 mM potassium phosphate buffer (pH 6.0), 1.34% YNB, $4 \times 10^{-5}\%$ biotin, 0.5% methanol;

LB-AMP medium: 0.5% yeast extract, 1% peptone, 1% NaCl, 100 μg/mL ampicillin, pH 7.0;

LB-AMP plate: 0.5% yeast extract, 1% peptone, 1% NaCl, 1.5% agar, 100 μg/mL ampicillin, pH 7.0;

Upper layer medium (plate): 0.1% $MgSO_4$, 1% $KH_2PO_4$, 0.6% $(NH_4)_2SO_4$, 1% glucose, 18.3% sorbitol, 0.35% agarose;

Lower layer medium (plate): 2% glucose, 0.5% $(NH_4)_2SO_4$, 1.5% $KH_2PO_4$, 0.06% $MgSO_4$, 0.06% $CaCl_2$, 1.5% agar.

The present invention will be further illustrated below with reference to the examples.

Example 1 Screening of Heat-Resistant Mutants

Mutations were performed at 10 sites (W46E, Q62W, G70E, A73P, T114H, N137V, D142R, S146E, R159Y, Y255D) of the wild-type phytase APPA (whose amino acid sequence was SEQ ID NO: 1, and encoding nucleotide sequence was SEQ ID NO: 2) to obtain a phytase mutant APPA-M0, whose amino acid sequence was SEQ ID NO: 3, with reference to which an encoding nucleotide sequence was synthesized as SEQ ID NO: 4. Compared with phytase APPA, the heat resistance of mutant APPA-M0 was significantly improved. After treatment at 75° C. for 5 min, the residual enzyme activity of APPA was less than 10%, while the residual enzyme activity of APPA-M0 was higher than 85%.

In order to further improve the heat resistance of the phytase mutant APPA-M0, protein structure analysis was carried out. This protein has two domains: domain 1 constituted by 134 amino acid residues at the N-terminal and 152 amino acid residues at the C-terminal, and domain 2 constituted by the remaining 124 amino acid residues in the middle, wherein the conserved sequence and activity center were both located in domain 1. Further mutations were performed without destroying the secondary structure and activity center of the protein.

1.1 Design of PCR Primers M0-F1, M0-R1:
- M0-F1: GGCGAATTCCAGTCAGAACCAGAGTTGA-AGTT, SEQ ID NO: 27 (The restriction enzyme EcoRI recognition site is underlined);
- M0-R1: ATAGCGGCCGCTTACAAGGAACAAGCA-GGGAT, SEQ ID NO: 28 (The restriction enzyme NotI recognition site is underlined).

APPA-M0 gene (SEQ ID NO: 4) was served as the template, and the above primers were used to perform PCR amplification by GeneMorph II Random Mutation PCR Kit (Stratagene), followed by recovering the PCR product from gel. After digested with EcoRI and NotI, the PCR product was ligated into pET21a vector that was subjected to the same digestion. The resulting vector was transformed into *Escherichia coli* BL21 (DE3), then the transformed *Escherichia coli* was spread on LB+Amp plate, and cultured upside down at 37° C. After the transformants appeared, the colonies were picked one by one into a 96-well plate with a toothpick. 150 μl of LB+Amp medium containing 0.1 mM IPTG was added to each well to culture the cells at 37° C. at 220 rpm for about 6 hours. Then the culture was centrifuged, the supernatant was discarded, and the cells were resuspended with buffer, frozen and thawed repeatedly to break the cells to obtain phytase-containing cell lysate from *Escherichia coli*.

40 μl of lysate was taken into two new 96-well plates respectively, and one of the 96-well plates was treated at 75° C. for 5 min; then each of the two 96-well plates was added with 80 μl of substrate to react at 37° C. for 30 min, then added with 80 μl of stop solution (ammonium vanadate: ammonium molybdate:nitric acid=1:1:2), and the content of the generated inorganic phosphorus was measured. Different mutants maintained different activities after the high temperature treatment.

The experimental results show that some mutations had no effect on the heat resistance of phytase APPA-M0, some mutations even made the heat resistance or enzyme activity of phytase APPA-M0 worse. In addition, although some mutations can improve the temperature resistance of APPA-M0, they also significantly changed the enzymatic properties of APPA-M0. Such mutations are not in line with the requirements. Finally, mutation sites that can significantly improve the heat resistance of APPA-M0 without affecting its enzymatic activity and original enzymatic properties: A36P, N126E, V211W, Q253Y, Q258E and S266P, were obtained.

On the basis of phytase APPA-M0, the present invention provides single-site mutants comprising one mutation site selected from A36P, N126E, V211W, Q253Y, Q258E, and S266P, which are respectively named as PHY-M1, PHY-M2, PHY-M3, PHY-M4, PHY-M5, and PHY-M6, the amino acid sequences of which are set forth in SEQ ID NO:5, SEQ ID NO:7, SEQ ID NO:9, SEQ ID NO:11, SEQ ID NO:13, and SEQ ID NO: 15, respectively, and their encoding nucleotide sequences are set forth in SEQ ID NO: 6, SEQ ID NO: 8, SEQ ID NO: 10, SEQ ID NO: 12, SEQ ID NO: 14, and SEQ ID NO: 16, respectively.

The present invention further provides mutants comprising a combination of two mutation sites selected from A36P/V211W, A36P/Q253Y, and V211W/Q253Y, which are named as PHY-M7, PHY-M8, and PHY-M9, respectively, the amino acid sequences of which are set forth in SEQ ID NO: 17, SEQ ID NO: 19, and SEQ ID NO: 21, respectively, and their encoding nucleotide sequences are set forth in SEQ ID NO: 18, SEQ ID NO: 20, and SEQ ID NO: 22, respectively.

The present invention also provides a mutant comprising a combination of three mutation sites A36P/V211W/Q253Y, which is named as PHY-M10, the amino acid sequence of which is set forth in SEQ ID NO: 23, and its encoding nucleotide sequence is set forth in SEQ ID NO: 24.

The present invention also provides a mutant comprising a combination of four mutation sites A36P/N126E/V211W/Q253Y, which is named as PHY-M11, the amino acid sequence of which is set forth in SEQ ID NO: 25, and its encoding nucleotide sequence is set forth in SEQ ID NO:26.

Example 2 Expression of Phytase Mutants in *Pichia pastoris*

According to the codon preference of *Pichia pastoris*, the gene sequence of APPA-M0 as shown in SEQ ID NO: 4 were optimized and synthesized, and two restriction sites of enzymes EcoRI and NotI were added to the 5' and 3' ends of the synthetic sequence, respectively.

2.1 Construction of Expression Vector

The synthesized gene sequences of APPA-M0 and mutants were digested with EcoRI and NotI, respectively, and then ligated into pPIC-9K vector that was digested with the same enzymes at 16° C. overnight. The resulting vector was transformed into *Escherichia coli* DH5a, then the transformed *Escherichia coli* cells were spread on LB+Amp plate, and cultured upside down at 37° C. After the transformants appeared, colony PCR was performed (reaction system: single colony picked from the plate as template, 0.5 μl of rTaqDNA polymerase, 2.0 μL of 10×Buffer, 2.0 μL of dNTPs (2.5 mM), 0.5 μL of 5'AOX primer (10M), 0.5 μL of 3'AOX primer, 14.5 μL of ddH₂O 14.5 μL; reaction program: pre-denaturation at 95° C. for 5 min; 30 cycles: 94° C. for 30 sec, 55° C. for 30 sec, 72° C. for 2 min; 72° C. for 10 min. The positive clones were verified by sequencing to obtain the correct recombinant expression plasmids.

2.2 Construction of Engineered *Pichia pastoris* Strains 2.2.1 Preparation of Competent Cells of *Pichia pastoris*

The *Pichia pastoris* GS115 strain was activated on an YPD plate, and cultured at 30° C. for 48 h. Then an activated GS115 colony was inoculated into 6 mL of YPD liquid medium at 30° C. at 220 rpm for about 12 hours. Then the broth culture was transferred to a conical flask containing 30 mL of YPD liquid medium, and cultured at 30° C. at 220 rpm for about 5 hours. The cell density was detected by a UV spectrophotometer. When the OD600 value was in the range of 1.1-1.3, the culture was centrifuged at 9000 rpm, 4° C. for 2 min. 4 mL of cells were collected into a sterilized EP tube, the supernatant was gently discarded, and the remaining supernatant was removed with sterilized filter paper. The collected cells were resuspended with 1 mL of pre-cooled sterile water, and centrifuged at 4° C., 9,000 rpm for 2 min, and the supernatant was gently discarded. The cells were washed with 1 mL of sterile water again, centrifuged at 9,000 rpm, 4° C. for 2 min, and the supernatant was gently discarded. The cells were resuspended with 1 mL of pre-cooled sorbitol (1 mol/L), centrifuged at 9000 rpm, 4° C. for 2 min, the supernatant was gently discarded, and the cells were gently resuspended with 100-150 µl of pre-cooled sorbitol (1 mol/L).

2.2.2 Transformation and Screening

The expression plasmids constructed in 2.1 were linearized with Sac I, the linearized fragments were purified and recovered, and then transformed into *Pichia pastoris* GS115 by electroporation. The transformed *Pichia pastoris* was screened on a MD plate to obtain the recombinant strains of *Pichia pastoris*. Transformants carrying multiple copies were screened on YPD plates containing different concentrations of geneticin (0.5 mg/mL-8 mg/mL).

The obtained transformants were respectively transferred into BMGY medium, cultured at 30° C. by shaking at 250 rpm for 1d, then transferred into BMMY medium, cultured at 30° C. by shaking at 250 rpm, and 0.5% methanol was added to the culture every day to induce expression for 4d. The cells were removed by centrifugation at 9000 rpm for 10 min and fermentation supernatants containing phytase APPA-M0 and phytase mutants were obtained respectively.

(1) Definition of Enzyme Activity Unit

Under the conditions of temperature of 37° C. and pH of 5.0, the release of 1 µmol of inorganic phosphorus from sodium phytate with a concentration of 5.0 mmol/L per minute is defined as one unit of enzyme activity, which is represented by U.

(2) Method of Measuring Enzyme Activity 1.8 mL of acetic acid buffer (pH 5.0) and 0.2 mL of sample reaction solution were added into two 25 mL colorimetric tubes A and B, and mixed well, and the resulting mixtures were preheated at 37° C. for 5 min. 4 mL of substrate solution was added to the tube A, 4 mL of stop solution was added to the tube B, and both of them were respectively mixed well to react at 37° C. for 30 min. After the reaction was completed, 4 mL of stop solution was added to the tube A, 4 mL of substrate solution was added to the tube B, and both of them were respectively mixed well. The resulting mixtures were stood for 10 min, and the absorbance values thereof were measured at 415 nm wavelength. Three parallels were made for each sample, the average value of absorbance values was recorded, and the enzyme activity of phytase was calculated by the linear regression equation through the standard curve.

Enzyme activity X=F×C/(m×30), wherein: X—unit of enzyme activity, U/g (mL);

F—the total dilution fold of the sample solution before the reaction;

C—enzyme activity calculated by the linear regression equation according to the absorbance value of the actual sample solution, U;

M—sample mass or volume, g/mL;

30—duration of reaction time.

The fermentation supernatants of the *Pichia pastoris* recombinant strains constructed above were respectively tested for enzyme activity using the above method.

Example 3 Expression of Phytase Mutants in *Trichoderma reesei*

According to the codon preference of *Trichoderma*, the gene sequence of APPA-M0 as shown in SEQ ID NO: 4, and the gene sequences of the mutants were optimized and synthesized, and two restriction sites of KpnI and MluI were added to the 5' and 3' ends of the synthetic sequences, respectively.

3.1 Construction of Expression Vector

The synthesized gene fragment of phytase and pSC1G vector were digested with restriction enzymes KpnI and MluI (Fermentas), respectively, and the digested products were purified using a gel purification kit. The digested products of the above-mentioned phytase gene and the pSC1G vector were ligated using T4 DNA ligase (Fermentas), the resulting vector was transformed into *Escherichia coli* Trans5α (Transgen), the transformed *Escherichia coli* Trans5α was screened with ampicillin, and the clones were verified by sequencing (Invitrogen). When the clone has a correct sequence, the recombinant plasmid containing the phytase gene was then obtained.

3.2 Construction of *Trichoderma reesei* Recombinant Strains (1) Preparation of Protoplast UE spore suspension of the host *Trichoderma reesei* was inoculated on a PDA plate, and cultured at 30° C. for 6 days. When the spores were abundant, a colony block of about 1 cm×1 cm was cut, placed in a liquid medium containing 120 mL of YEG+U (0.5% yeast powder, 1% glucose, 0.1% uridine), and cultured at 30° C. with shaking at 220 rpm for 14-16 h.

The mycelium was collected by filtration with sterile gauze, and washed once with sterile water. The mycelium was placed in a conical flask containing 20 mL of 10 mg/mL lyase solution (Sigma L1412), and kept at 30° C. at 90 rpm for 1-2 h. The progress of protoplast transformation was observed and detected using a microscope.

20 mL of pre-cooled 1.2 M sorbitol (1.2 M sorbitol, 50 mM Tris-Cl, 50 mM CaCl$_2$)) was added into the above conical flask, which was shaken evenly gently, the resulting mixture was filtered with a sterile Miracloth to collect the filtrate, then the collected filtrate was centrifuged at 3000 rpm, 4° C. for 10 min; the supernatant was discarded, the cells were suspended with 5 mL of pre-cooled 1.2 M sorbitol solution, then the cell solution was centrifuged at 3000 rpm at 4° C. for 10 min; the supernatant was discarded, the cells were suspended with an appropriate amount of pre-cooled 1.2 M sorbitol, and the suspension solution was aliquoted (200 µL/tube, the concentration of protoplast was 108/mL).

(2) Transformation of Expression Vector

The following operations were all performed on ice. 10 µg of the recombinant plasmids constructed above was respectively added to a 7 mL sterile centrifuge tube containing 200 µL of protoplast solution, then the obtained mixture was added with 50 µL of 25% PEG (25% PEG, 50 mM Tris-Cl, 50 mM CaCl$_2$)), and mixed well by flicking the bottom of the tube. The resulting mixture was placed on ice for 20 min, added with 2 mL of 25% PEG, and mixed well. The obtained mixture was kept at room temperature for 5 min, added with 4 mL of 1.2 M sorbitol and mixed well gently. The mixture was poured into the upper layer medium that had been melted and kept at 55° C., and mixed well gently, then the mixture was spread on the prepared plate with lower layer medium, incubated at 30° C. for 5-7 d until transformants grew out. The grown transformants were picked to a plate with the lower layer medium for re-screening, and the colony with a relatively smooth edge was a positive transformant.

According to the above method, the engineered recombinant *Trichoderma reesei* expressing APPA-M0 and phytase mutants were constructed and obtained respectively.

(3) Fermentation Verification and Enzyme Activity Assay

The engineered strains of *Trichoderma reesei* constructed above were respectively inoculated to PDA solid plates, and cultured upside down in a 30° C. constant temperature incubator for 6-7 days. When the spores were abundant, two blocks of mycelium with a diameter of 1 cm were taken and inoculated into a 250 ml conical flask containing 50 mL of fermentation medium (1.5% glucose, 1.7% lactose, 2.5% corn syrup, 0.44% $(NH_4)_2SO_4$, 0.09% $MgSO_4$, 2% $KH_2PO_4$, 0.04% $CaCl_2$, 0.018% Tween-80, 0.018% trace elements) respectively, cultured at 30° C. for 48 hours and then at 25° C. for 48 hours. The fermentation medium was centrifuged to obtain fermentation supernatants containing phytase APPA-M0 and the above-mentioned phytase mutants respectively.

The fermentation supernatants from the recombinant strain of *Trichoderma reesei* were tested for enzyme activity of phytase using the method described in Example 2.

Example 4 Thermal Stability Analysis

The fermentation supernatants of the recombinant strains expressing the phytase mutants obtained above were diluted 10-fold with 0.25M sodium acetate buffer (pH 5.0) pre-heated for 10 min. The diluted samples were treated at 80° C. for 5 min, or treated at 85° C. for 5 min, respectively. When the treatment was completed, the samples were taken and cooled to room temperature. The phytase enzyme activity of the samples after heat treatment was measured respectively, and the enzyme activity of the untreated sample was set as 100% to calculate the residual enzyme activity of the samples after heat treatment. The specific results are shown in Table 1 and Table 2.

Residual enzyme activity (%)=enzyme activity of samples after heat treatment/enzyme activity of untreated samples×100%.

TABLE 1

| Analysis of heat resistance of phytase mutants at 80° C. | |
| --- | --- |
| Phytase mutant | Residual enzyme activity after treatment at 80° C. for 5 min |
| APPA-M0 | 45.05% |
| PHY-M1 | 49.07% |
| PHY-M2 | 60.00% |
| PHY-M3 | 81.91% |
| PHY-M4 | 70.51% |
| PHY-M5 | 52.95% |
| PHY-M6 | 52.33% |
| PHY-M7 | 84.95% |
| PHY-M8 | 72.57% |
| PHY-M9 | 88.42% |

TABLE 1-continued

| Analysis of heat resistance of phytase mutants at 80° C. | |
| --- | --- |
| Phytase mutant | Residual enzyme activity after treatment at 80° C. for 5 min |
| PHY-M10 | 95.22% |
| PHY-M11 | 99.63% |

As can be seen from the results in Table 1, compared with phytase APPA-M0, after the phytase mutants PHY-M1, PHY-M2, PHY-M3, PHY-M4, PHY-M5, and PHY-M6, which contains a single mutation A36P, N126E, V211W, Q253Y, Q258E, and S266P respectively, were treated at 80° C. for 5 min, the residual enzyme activity thereof was generally increased by 8.9%-121.2%. Thus, the mutation sites A36P, N126E, V211W, Q253Y, Q258E and S266P provided by the present invention significantly improve the heat resistance of phytase.

Compared with the corresponding mutants with single mutation site, the phytase mutants PHY-M7, PHY-M8, and PHY-M9 containing a combination of two mutation sites A36P/V211W, A36P/Q253Y, and V211W/Q253Y, respectively, the phytase mutant PHY-M10 containing a combination of three mutation sites A36P/V211W/Q253Y, and the phytase mutant PHY-M11 containing a combination of four mutation sites A36P/N126E/V211W/Q253Y all had further improved heat resistance, showing unexpected technical effects.

TABLE 2

| Analysis of heat resistance of phytase mutants at 85° C. | |
| --- | --- |
| Phytase mutant | Residual enzyme activity after treatment at 85° C. for 5 min |
| APPA-M0 | 43.49% |
| PHY-M2 | 50.98% |
| PHY-M3 | 52.87% |
| PHY-M7 | 55.20% |
| PHY-M9 | 62.26% |
| PHY-M10 | 69.51% |
| PHY-M11 | 74.60% |

Among them, after the phytase mutants PHY-M2 and PHY-M3 containing a single mutation site N126E and V211W, the phytase mutants PHY-M7 and PHY-M9 containing a combination of two mutation sites A36P/V211W and V211W/Q253Y, the phytase mutant PHY-M10 containing a combination of three mutation sites A36P/V211W/Q253Y, and the phytase mutant PHY-M11 containing a combination containing of four mutation sites A36P/N126E/V211W/Q253Y were treated at 85° C. for 5 minutes, the residual enzyme activities still maintain 50.98-74.60%, which was 17.2%-71.5% higher than that of APPA-M0, indicating a stronger heat resistance.

To sum up, the heat resistance of the phytase mutants provided by the present invention is significantly improved, which is beneficial to the wide application of phytase in feed.

The invention claimed is:

1. A phytase mutant, wherein the mutant comprises an amino acid sequence having at least 90% identity with SEQ ID NO: 3, and comprises an amino acid substitution of Q253 Y.

2. The mutant according to claim 1, wherein the amino acid sequence of the mutant has at least 91%, 92%, 93%, 94%, 95%, 96%, 97%, 98%, or at least 99% identity with SEQ ID NO:3.

3. The mutant according to claim 1, wherein the amino acid sequence of the mutant has at least 99.1%, 99.2%, 99.3%, 99.4%, 99.5%, 99.6%, 99.7%, 99.8%, or at least 99.9% identity with SEQ ID NO:3.

4. The mutant according to claim 1, wherein the mutant further comprises at least one amino acid substitution selected from the group consisting of A36P, N126E, V211W, Q258E, and S266P.

5. The mutant according to claim 4, wherein the combination of substitutions contained in the mutant is selected from the group consisting of A36P/Q253Y, V211W/Q253Y, A36P/V211W/Q253Y and A36P/N126E/V211W/Q253Y.

6. The mutant according to claim 1, wherein the mutant further comprises an amino acid substitution compared with SEQ ID NO: 3 at at least one position selected from the group consisting of 36, 126, 211, 258, and 266.

7. A DNA molecule encoding the phytase mutant according to claim 1.

8. A vector comprising the DNA molecule according to claim 7.

9. A host cell comprising the vector according to claim 8.

* * * * *